(12) United States Patent
Kleyman et al.

(10) Patent No.: US 11,464,562 B1
(45) Date of Patent: Oct. 11, 2022

(54) END EFFECTOR STRUCTURE FOR TISSUE ABLATION

(71) Applicants: Gennady I Kleyman, Brooklyn, NY (US); Annaniy Berensteyn, Edgewater, NJ (US)

(72) Inventors: Gennady I Kleyman, Brooklyn, NY (US); Annaniy Berensteyn, Edgewater, NJ (US)

(73) Assignee: Expandoheat, L.L.C., Atlantic Heights, NJ (US)

( * ) Notice: Subject to any disclaimer, the term of this patent is extended or adjusted under 35 U.S.C. 154(b) by 688 days.

(21) Appl. No.: 16/367,461

(22) Filed: Mar. 28, 2019

Related U.S. Application Data

(60) Provisional application No. 62/651,296, filed on Apr. 2, 2018.

(51) Int. Cl.
*A61B 18/18* (2006.01)
*A61B 18/08* (2006.01)
*A61B 18/14* (2006.01)

(52) U.S. Cl.
CPC ...... *A61B 18/1445* (2013.01); *A61B 18/1815* (2013.01); *A61B 2018/183* (2013.01); *A61B 2018/1861* (2013.01)

(58) Field of Classification Search
CPC ............ A61B 18/1445; A61B 18/1815; A61B 2018/183; A61B 2018/1861; A61B 2018/00077; A61B 18/18; A61B 2018/00351; A61B 2018/00422; A61B 2018/00452; A61B 2018/00488; A61B 2018/00494; A61B 2018/00505; A61B 2018/00511; A61B 2018/00517; A61B 2018/00523; A61B 2018/00529; A61B 2018/00547; A61B 2018/00559; A61B 2018/00577; A61B 2018/00702; A61B 2018/00726; A61B 2018/00791; A61B 2018/00839; A61B 2018/00875; A61B 2018/00982; A61B 2018/00994;
(Continued)

(56) References Cited

U.S. PATENT DOCUMENTS

| | | | | |
|---|---|---|---|---|
| 5,496,271 A | * | 3/1996 | Burton | A61B 18/18 604/113 |
| 7,052,491 B2 | * | 5/2006 | Erb | A61B 18/1402 606/17 |
| 2015/0313670 A1 | * | 11/2015 | Shroff | A61B 18/18 606/33 |

* cited by examiner

*Primary Examiner* — Michael F Peffley
*Assistant Examiner* — Amanda L Zink

(57) ABSTRACT

An end effector structure for tissue ablation powered by microwave energy source and end effector including a microwave antenna surrounded by a segments from microwave absorbing materials. Microwave absorbing material is a material, transparent to microwave energy impregnated with microwave absorbing particles, and has differing microwave transmission and/or absorption characteristics at different locations along the microwave antenna to apply to the desired bi-tissue, a selective amount of microwave and/or heat energy. Microwave transparent material can be ceramic, silicone, fluorosilicone, fluorocarbon, thermoplastic rubber, ethyline propylene diene monomer, urethane etc. Microwave absorbing particles can be from nickel (Ni), copper (Cu), Aluminum (Al), Ag/Cu; Ag/Al; Ag/Ni; Ag/Glass, nickel-plated graphite, silver-plated aluminum, silver-plated copper, silver-plated nickel, silver-plated glass and pure silver etc.

13 Claims, 4 Drawing Sheets

(58) Field of Classification Search
CPC .... A61B 2018/1846; A61B 2018/1853; A61B 2018/1869
See application file for complete search history.

END EFFECTOR STRUCTURE FOR TISSUE ABLATION

BACKGROUND OF THE INVENTION

1. Field of the Invention

The invention relates to an inflatable tissue-treating device for tissue ablation, such as ablation of an artery, vein and tissue.

2. Background of the Invention

In some previous microwave tissue ablation devices that have an elongated probe having a proximal access end and an opposite distal penetration end, such ablation devices are adapted to penetrate into bio-tissue via an insert passage extending there through from the access end to the penetration end thereof. The ablation device further includes an internal antenna coupled to a transmission line connected to a microwave or RF frequency power source, for generating an electric field sufficiently strong to cause bio-tissue ablation. The antenna and the transmission line each have a transverse cross-sectional dimension adapted for sliding receipt through the insert passage while the elongated probe is positioned in the bio-tissue. Such sliding receipt occurs until the antenna device is advanced to a position beyond the penetration end and further into the bio-tissue.

In those prior microwave ablation devices, a maximum of microwave energy delivered at the point where an inner conductor of coaxial cable exits from coaxial cable and is connected to a microwave antenna. In this location, tissue will receive a maximum energy. However, for many procedures, the desired target for ablation (ex. Cancerous cells) is not located in this area and does not receive the desired (e.g. maximum) distribution of ablating energy.

It is desirable to provide a controlled distribution of ablating microwave energy (e.g. more equally by length of end effector with microwave antenna or customize profile of thermal ablation) to ablate all targeted tissue and minimize thermal damage of healthy tissue.

SUMMARY OF THE INVENTION

The present invention addresses at least the above-described problems and/or disadvantages and provides at least the advantages described below.

An exemplary embodiment of the present invention provides an end effector structure for tissue ablation powered by microwave energy source and end effector including a microwave antenna surrounded by segments from microwave absorbing materials. Microwave absorbing material is a material, transparent to microwave energy impregnated with microwave absorbing particles, and has differing microwave transmission and/or absorption characteristics at different locations along the microwave antenna to apply to the desired bio-tissue, a selective amount of microwave and/or heat energy. Microwave transparent material can be ceramic, silicone, fluorosilicone, fluorocarbon, thermoplastic rubber, ethyline propylene diene monomer, urethane etc. Microwave absorbing particles can be from nickel (Ni), copper (Cu), Aluminum (Al), Ag/Cu; Ag/Al; Ag/Ni; Ag/Glass, nickel-plated graphite, silver-plated aluminum, silver-plated copper, silver-plated nickel, silver-plated glass and pure silver etc.

Volume resistivity is a fundamental property that quantifies how strongly a given material opposes the flow of electric current. A low resistivity indicates a material that readily allows the flow of electric current. The international system unit of volume resistivity is the ohm-meter (Ω-m) or ohm-centimeter (ohm-cm). In case of microwave absorbing materials, when volume resistivity is high it means there are fewer microwave absorbing particles (fillers) in the microwave absorbing material and, correspondingly, less microwave energy will transfer into the heat energy and more microwave energy will be transmitted outside of microwave absorbing material. If the volume resistivity is low, it means there are more microwave absorbing particles (fillers) in the microwave absorbing material and less microwave energy will be transmitted outside of microwave absorbing and more microwave energy will be transferred into the heat energy.

When the microwave antenna, surrounded by a segment from microwave absorbing material, emits microwave energy, the segment made from microwave absorbing material with high density of microwave absorbing particles will transfer higher percentage of microwave energy into the heat energy and lower percentage of microwave energy will be transmitted thru the microwave absorbing segment. In this example, layers of tissue that are in contact with the segment will be heated by conduction from hot surface of the segment while the deeper layers of the tissue will receive less of transmitted microwave energy.

When the microwave antenna, surrounded by a segment from microwave absorbing material that extends to an outer region or surface that typically engages a surface of the bio-tissue to be selectively ablated, emits microwave energy and the segment is made from microwave absorbing material with low density of microwave absorbing particles, it will transfer lower percentage of microwave energy into the heat energy and therefore a higher percentage of microwave energy will be transmitted thru the microwave absorbing segment into the surrounding bio-tissue. In this example, the layers of tissue that are in contact with the segment will receive less microwave energy and will be heated by heat conduction from the hot surface of the segment while the deeper (more distal from the antenna) layers of the tissue will receive more of the transmitted microwave energy.

According to the embodiments of this invention, placing segments of selected dimension microwave absorbing material with different selected density of particles around a microwave antenna allows to achieve different and controlled patterns of tissue ablation by adjusting the percentage of microwave energy that is transformed into the heat energy and heats the tissue layers in direct contact with the end effector by heat conduction, and by the microwave energy that is transmitted through the microwave absorbing material to penetrate and ablate the deeper layers of the tissue by direct application of microwave energy radiated from the antenna.

According to the another embodiments of this invention, placing segments of selected dimension microwave absorbing material and material transparent to microwave energy around a microwave antenna allows to achieve different and controlled patterns of tissue ablation by heating the tissue layers in direct contact with end effector by heat conduction and by the microwave energy that is transmitted through the microwave transparent material to penetrate and ablate the deeper layers of tissue by direct application of microwave energy radiated from the antenna.

According to the another embodiments of this invention, placing segments of selected dimension microwave absorbing material around a microwave antenna and block segment of this end effector by metal segment to block microwave energy and this allows ablate tissue outside this metal blocking segment.

According to the another embodiments of this invention, placing segments of selected dimension microwave absorbing material around a microwave antenna and cover this end effector with metal sleeve to block microwave energy allows all surrounded end effector tissue to be ablated only by conductive heat from end effector. All microwave energy will transfer to heat energy by microwave absorbing material.

DESCRIPTION OF REFERENCED ELEMENTS

2—cannula body (metal)
4, 14, 18, 28, 34, 44—insert made from microwave absorbing material with high density of particles
6, 16, 22, 24, 32, 46—insert from microwave absorbing material with low density of particles
8—coaxial cable
12—microwave antenna
26—spacer made from microwave transparent material (ex. Silicone, Nylon, ABS)
36—cannula
36A—cannula with portion to block contact of hot inserts with the tissue
52—thermally untreated tissue
54A-54R—thermally treated tissue
56A-56R—corresponding thermally treated tissue depth
58—thermal insulation material
62—end effector cap, made from metal, preferably stainless steel
64—insert, made from microwave absorbing material

BRIEF DESCRIPTION OF THE DRAWINGS

The above and other aspects, features and advantages of the present invention will become more apparent from the following detailed description when taken in conjunction with the accompanying drawing in which.

DETAILED DESCRIPTION OF THE PREFERRED EMBODIMENTS

Figure 1:
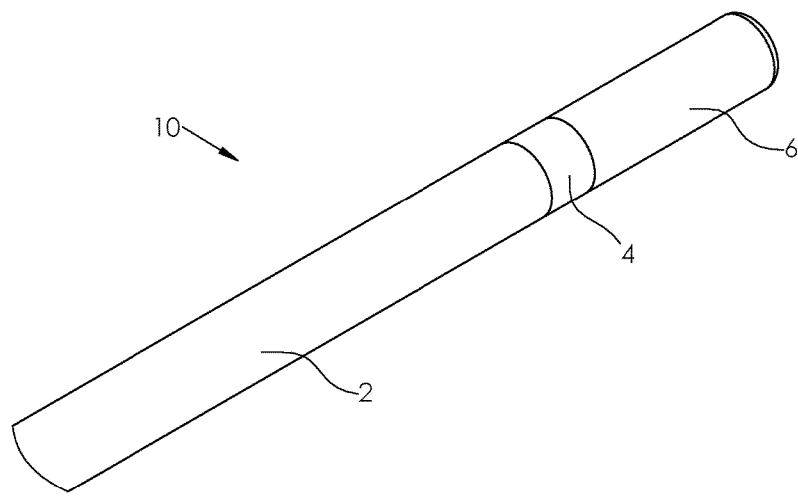
FIG. 1 illustrates an isometric view tissue-treating end effector of one embodiment of the present invention.

Various embodiments of the present invention are described in detail with reference to the accompanying drawings. Wherever possible, the same or similar reference numerals are used in the drawings and the description to refer to the same or like parts or steps. In the following description, specific details are provided to provide an overall understanding of embodiments of the present invention and those skilled in the art will recognize that various changes and modifications of the embodiments described herein can be made without departing from the scope and spirit of the invention. Descriptions of well-known functions and constructions are omitted for the sake of clarity and conciseness.

Figure 2:
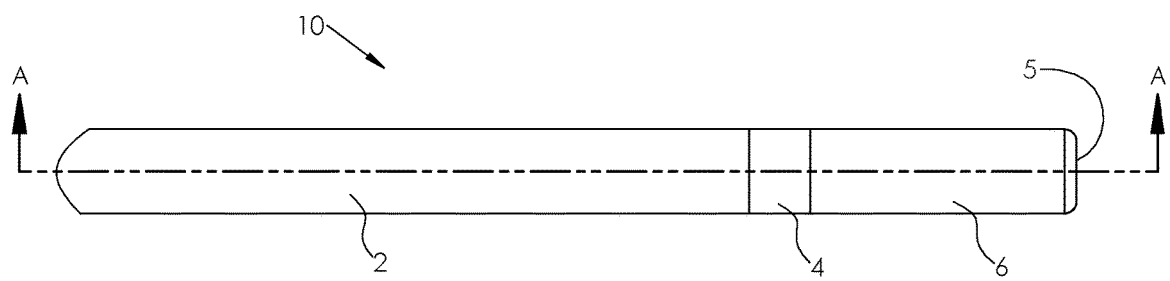
FIG. 2 illustrates an elevation view of the embodiment of FIG. 1 of the present invention.

FIG. 1 and FIG. 2 show general views of an end effector of a first embodiment of present invention. The first embodiment 10 of this invention as shown on in the sectional view of FIG. 3, the end effector including a microwave antenna 12 having a length, and is surrounded by the two segments 4, 6 (in this embodiment) made from microwave absorbing material.

Figure 3:
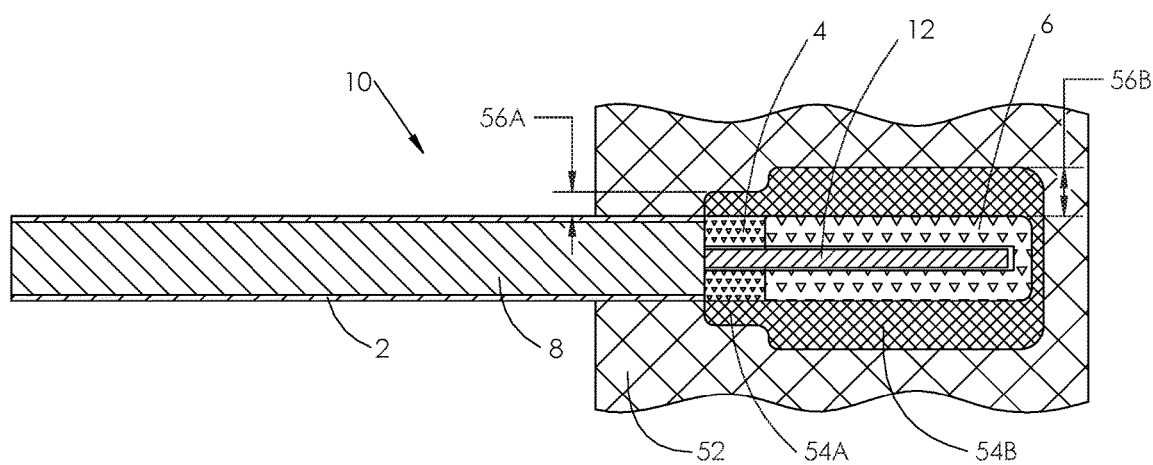
FIG. 3 shows a sectional view A-A of the embodiment of the present invention of FIG. 1.

In the sectional view of FIG. 3, in one embodiment, the microwave antenna is connected to the center conductor of a coaxial cable 8, held in a supporting cannula 2 and the cable is connected to a microwave power source (not shown) providing microwave power sufficient to cause the desired ablation. A first segment 4 is located distally from end 5 (end 5 is inserted into bio-tissue) of the end effector and is made from a microwave absorbing material with a high density of particles and segment 6, is located at the proximal to the end 5 of the end effector, is made from microwave absorbing material with a lower density of particles. When microwave antenna 12 emits microwave energy, the ablated tissue 54A, 54B and non-ablated tissue 52 will look like it is shown on FIG. 3 where the depth 56A of ablated tissue area 54A around segment 4 is less as compared to the depth 56B of the ablated tissue area 54B around segment 6. Segment 4 will transform most microwave energy into the heat energy and will heat mostly tissue layers in direct contact with the surface of segment 4, while segment 6 will allow more microwave energy to be transmitted through and ablate deeper layers of tissue by direct application of microwave energy through the less microwave absorbing segment 6. As an example, the segment 4 (with low volume resistivity) can be made from Ja-Bar Silicone Corporation material 807, which is made of silicone with silver particles dispersed inside it. This material has volume resistivity 0.010 ohm-cm, while segment 6 (with high volume resistivity) made from material 852 from Ja-Bar Silicone Corporation, which is made of silicone with nickel particles dispersed inside it, and it has volume resistivity of 2 ohm-cm. Additionally, the circumference and shape of the segments 4, 6 may be different and/or have a varied cross-section.

Figure 4:
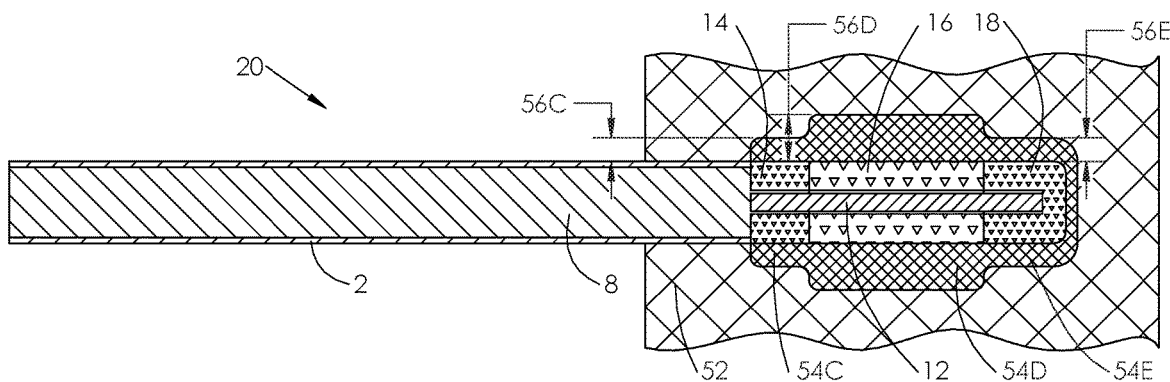
FIG. 4 shows a sectional view A-A of a second embodiment of the present invention.

As it is shown in the second embodiment 20 of FIG. 4, a microwave antenna 12 is surrounded by three segments 14, 16, and 18 made from a microwave absorbing material having different dimensions. The two segments 14 and 18 are located distally and proximally to end 5 and correspondingly and are made from a microwave absorbing material with low volume resistivity (e.g. by high particle density), while segment 16, located between segments 14 and 18, is made from a microwave absorbing material with high volume resistivity. When microwave antenna 12 emits microwave energy, the ablated tissue areas 54C, 54D, 54E and non-ablated tissue 52 will look like it is shown on FIG. 4 where the ablated tissue areas 54C and 54E around segments 14 and 18 respectively, are ablated less in depth 56C and 56E as compared to tissue area 54D around segment 16 having depth 56D.

Figure 5:
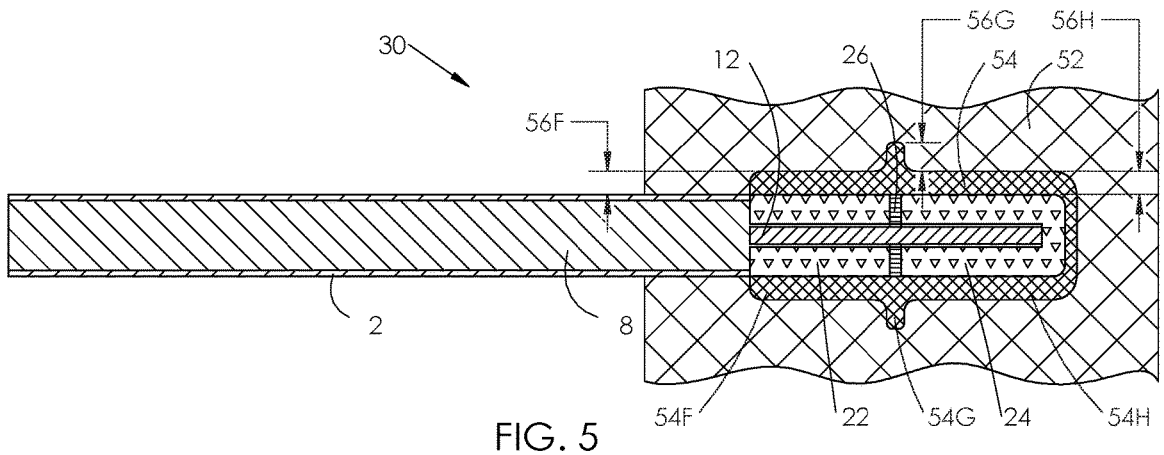
FIG. 5 shows a sectional view A-A of a third embodiment of the present invention.

As it shown in the third embodiment 30 of FIG. 5, the microwave antenna 12 is surrounded by three segments 22, 24, 26, and two of them—22 and 24—are made from a microwave absorbing material and segment 26 is made from a material, such as ceramic, nylon ABS, etc., that is transparent, or substantially transparent, to microwave energy. The transparent materials have no effect on microwave energy when microwaves pass thru them. Two segments 22 and 24 are placed on either side of segment 26, which is located between them. When the microwave antenna 12 emits microwave energy, the ablated tissue areas 54F, 54G, 54H and non-ablated tissue 52 will look like it is shown on FIG. 5 where ablated tissue area 54F an 54H around segments 22 and 24 are ablated less in depth (56F and 56H) as compared to tissue area around segment 26 having depth 56G, since the segment 26 does not absorb substantially any microwave energy.

Figure 6:
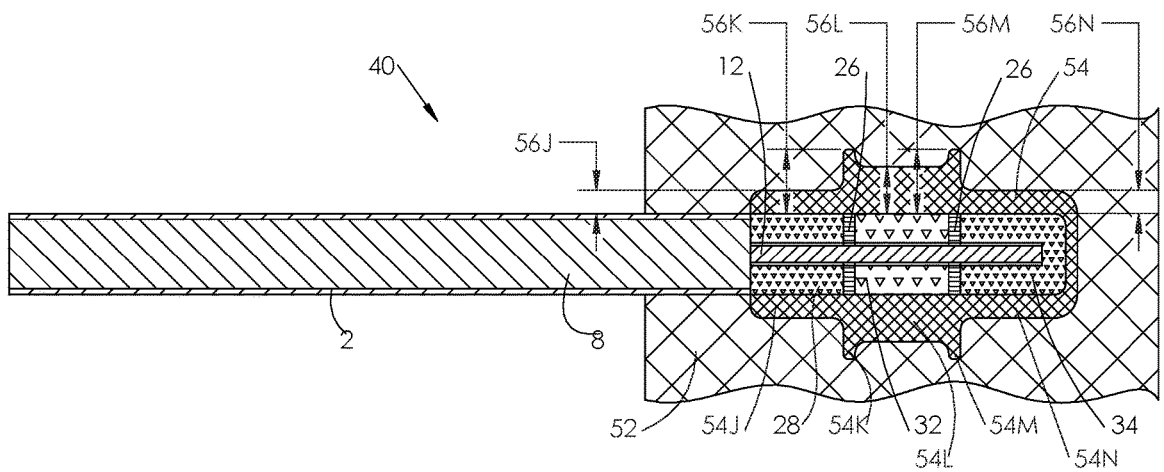
FIG. 6 shows a sectional view A-A of a fourth embodiment of the present invention.

The fourth embodiment 40 of the present invention is shown on FIG. 6, wherein the microwave antenna 12 is surrounded by five segments—two of them 28 and 34 made from a microwave absorbing material with low volume resistivity, with segment 32 made from a microwave absorbing material with high volume resistivity, while two other segments 26 are made from a material that is transparent to microwave energy. When the microwave antenna 12 emits microwave energy, the ablated tissue area 54 and the non-ablated tissue 52 will look like it is shown on FIG. 6. The ablated tissue areas 54J and 54N around segments 28 and 34, respectively, are ablated less in depth (56J and 56N respectively) as compared to the tissue area 54L having depth 56L around segment 32, and the ablated tissue area 54L around segment 32 is ablated less in depth 56L as compared to the ablated tissue areas 54K and 54M around segments 26 having depths 56K and 56M, respectively.

Figure 7:
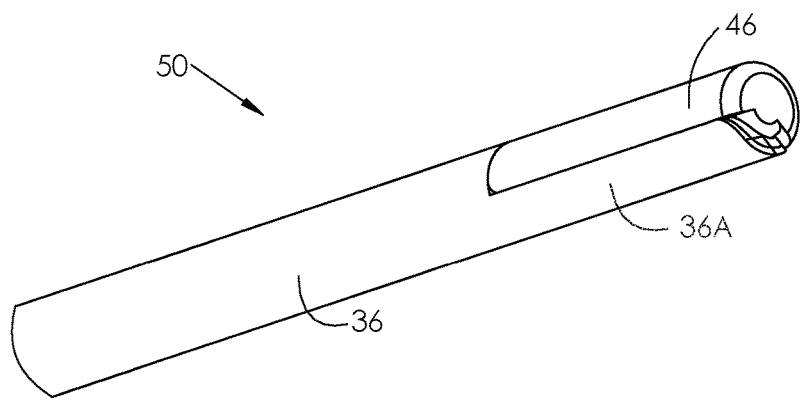
FIG. 7 illustrates an isometric view of tissue-treating end effector of the present invention of a fifth embodiment of the present invention.
Figure 8:
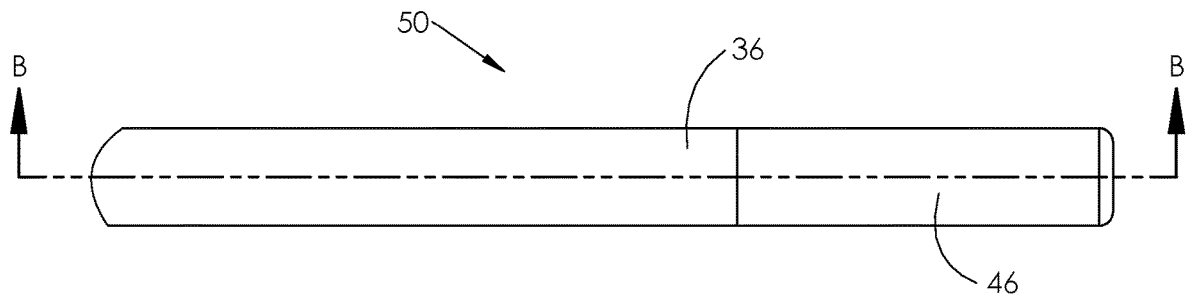
FIG. 8 illustrates a plan view tissue-treating end effector of the present invention of the fifth embodiment.
Figure 9:
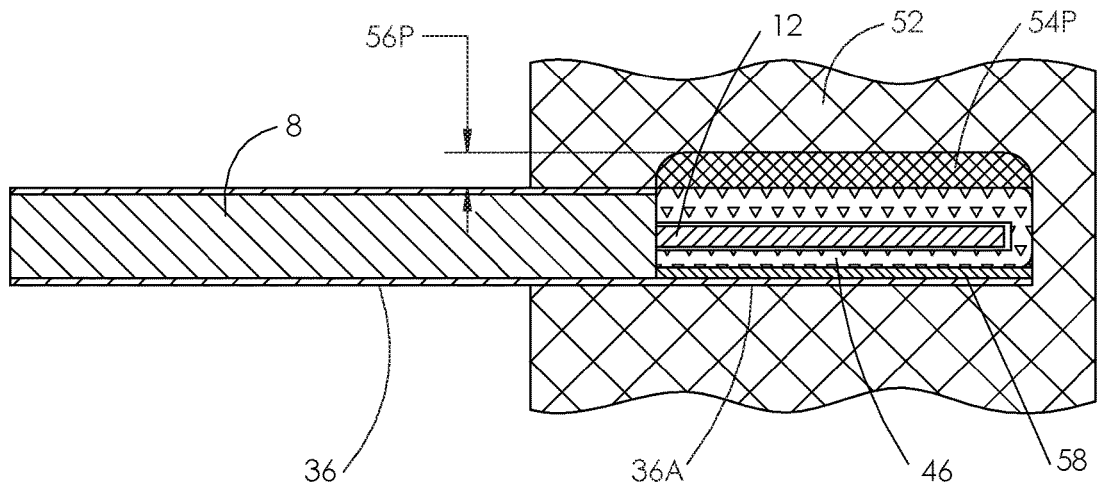
FIG. 9 shows a sectional view B-B of the fifth embodiment of invention.
Figure 10:
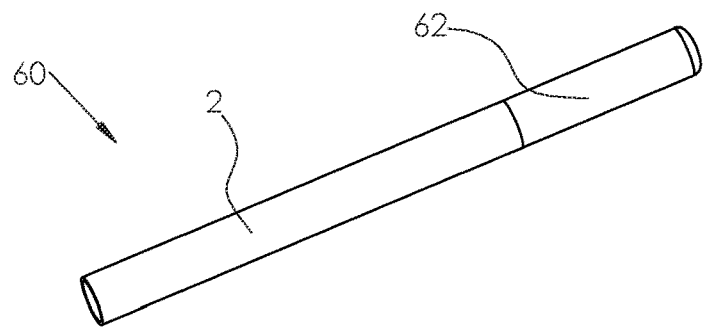
FIG. 10 illustrates an isometric view of tissue-treating end effector of the present invention of the sixth embodiment of the present invention.

The present invention includes embodiments having different segment configurations and/or dimensions radially around the antenna 12. For example, a fifth embodiment 50 of this invention is shown on FIG. 7, FIG. 8 and FIG. 9 that addresses the scenario when it is required to ablate some tissue area but without any thermal ablation effect to some other tissue area. As it is shown on FIG. 9, the microwave antenna 12 is surrounded by microwave absorbing material 46. A segment of the end effector, covered by metal segment 36A of cannula 36 (spaced apart from microwave antenna 12), and a thermal insulation material 58 which is positioned at least partially along the microwave absorbent material 46, and it also may be parallel to the microwave antenna at a selected distance between the segment 36A of cannula 36 and the microwave absorbing material 46. When microwave antenna 12 emits microwave energy, only the tissue area 54P which is not covered or shielded by the metal segment 36 and the thermal insulation material 56, will have a thermal effect from the end effector and be ablated to a selected depth 56P. The tissue area 52 will not have a thermal effect and thus have no ablation.

Figure 11:
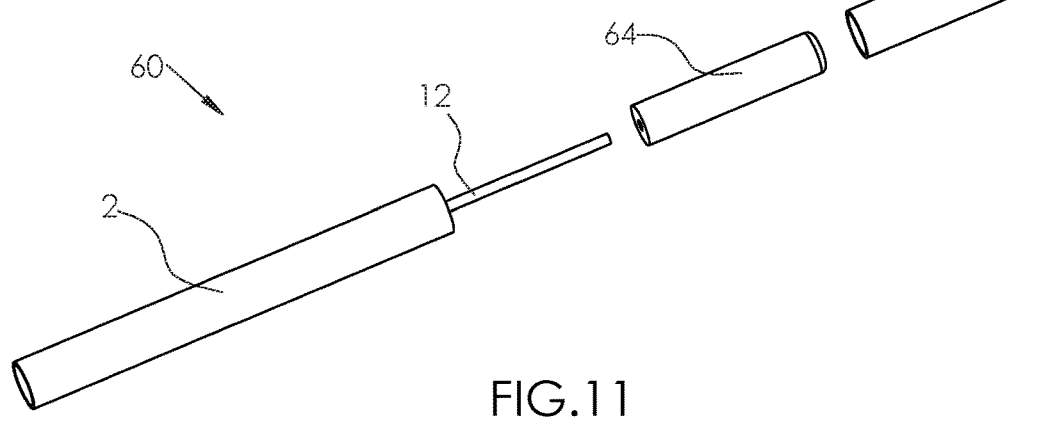
FIG. 11 illustrates an exploded view of tissue-treating end effector of the present invention of the sixth embodiment of the present invention.
Figure 12:
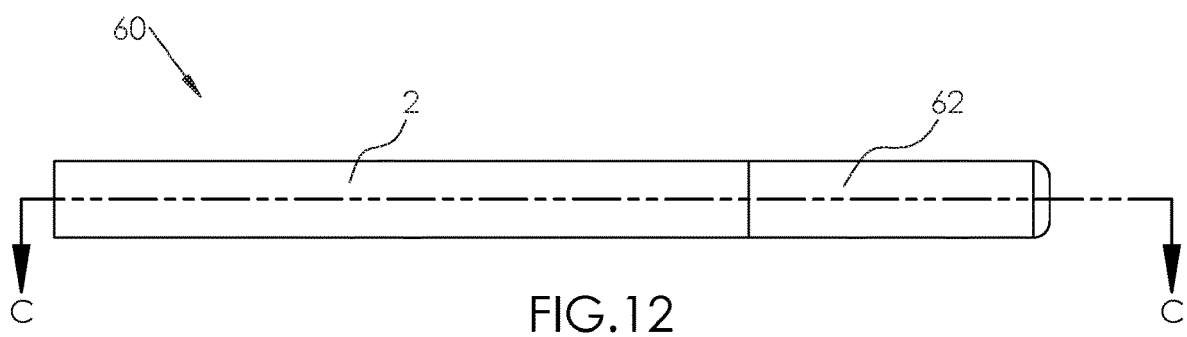
FIG. 12 illustrates a plan view tissue-treating end effector of the present invention of the sixth embodiment.
Figure 13:
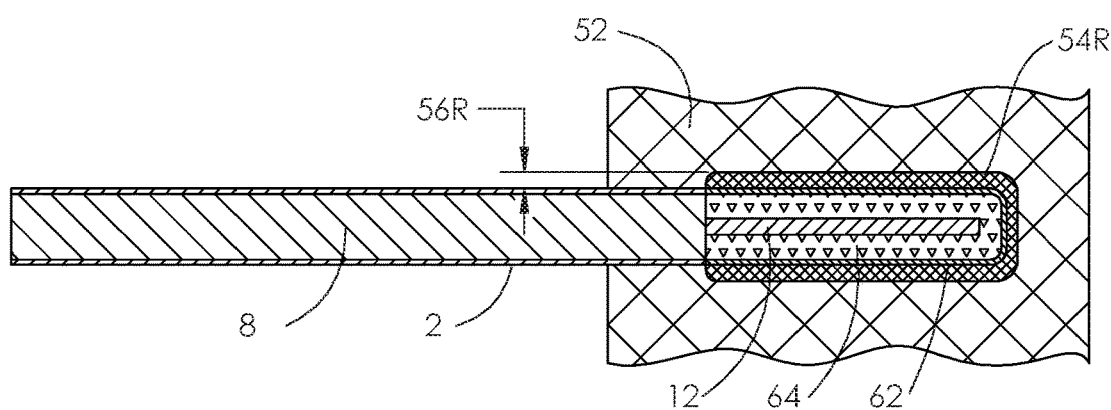
FIG. 13 shows a sectional view C-C of the sixth embodiment of invention.

The present invention includes embodiments having different segment configurations and/or dimensions radially around the antenna 12. For example, the sixth embodiment 60 of this invention is shown on FIG. 10, FIG. 11, FIG. 12 and FIG. 13 that addresses the scenario when it is required to ablate only a small amount of tissue that is in direct contacted with the end effector without heating and ablating deeper tissue areas. This heating of tissue which is in direct contact with the end effector is performed only by conduction of heat from the surface of the end effector (metal end effector cap 62) to the tissue in direct contacted with end effector. As it is best shown on FIG. 11 and FIG. 13, the microwave antenna 12 is surrounded by insert 64 made from microwave absorbing material, and the insert 64 is covered by the end effector cap 62 made from metal (preferably stainless steel). When the microwave antenna 12 emits microwave energy, the microwave absorbing material of insert 64 will convert microwave energy into the heat energy, thus heating the insert. The insert 64 then conducts the heat to the end effector cap 62. The end effector cap 62 will get heated and will ablate by conductivity of the tissue that is in direct contact with the end effector. Because the end effector cap 62 is made from metal, it will block microwave energy from escaping from the end effector and will prevent microwave energy from making any undesirable effects to the tissue and accordingly ablate bio-tissue 54R to a selected depth 56R around segment 62.

While the invention has been shown and described with reference to an exemplary embodiment thereof, it will be understood by those skilled in the art that various changes in form and details may be made therein without departing from the spirit and scope of the invention.

What is claimed is:

1. A tissue ablation apparatus to selectively ablate bio-tissue, comprising:
    an elongated end effector having an outer dimension, including
        an elongated microwave antenna extending along a length and having an end,
        a first microwave absorbing material emitting heat in response to microwave energy emitted from said microwave antenna, disposed in contact with said microwave antenna and disposed to provide heat to and allow microwave energy to said bio-tissue and having a first microwave absorption coefficient disposed along said elongated microwave antenna length and within said elongated end effector outer dimension at a first position relative said microwave antenna end,
        a second microwave absorbing material emitting heat in response to microwave energy emitted from said microwave antenna, disposed in contact with said microwave antenna and disposed to provide heat to and allow microwave energy to said bio-tissue and having a second microwave absorption coefficient disposed along said elongated microwave antenna length and within said elongated end effector outer dimension at a second position over said microwave antenna relative to said microwave antenna end different from said first microwave absorbing heat emitting material first position; and
    a support connected to said elongated end effector to provide axial and radial positioning of said elongated microwave antenna.

2. The tissue ablation apparatus of claim 1, wherein said first microwave absorbing material and said second microwave material are disposed at different positions along said elongated microwave antenna.

3. The tissue ablation apparatus of claim 1, further including a microwave transparent material disposed around said microwave antenna.

4. The tissue ablation apparatus of claim 1, wherein said first microwave absorbing material includes particles of microwave absorbing materials of different selected particle density and different microwave absorption from said second microwave absorbing material, wherein said first microwave absorbing material is disposed radially around said elongated microwave antenna.

5. The tissue ablation apparatus of claim 4, wherein a portion of said support extends at least partially along said outer dimension.

6. The tissue ablation apparatus of claim 1, further comprising a microwave energy conducting cable connected to said elongated microwave antenna.

7. The tissue ablation apparatus of claim 1, further comprising a metal cover disposed to partially cover said elongated end effector.

8. The tissue ablation apparatus of claim 1, further comprising a metal cover disposed to completely partially cover said elongated end effector.

9. A tissue ablation apparatus to selectively ablate biotissue, comprising:
   an elongated end effector having an outer dimension, including
      an elongated microwave antenna extending along a length, and
      a first microwave absorbing material having a first microwave absorption coefficient disposed along said elongated microwave antenna length and within said elongated end effector outer dimension;
   a tubular metal support connected to and surround said elongated end effector to provide axial and radial positioning of said elongated microwave antenna; and
   a microwave shield heated by said first microwave absorbing material and which extends at least partially along said elongated microwave antenna length and comprises a microwave shield material and formed to block outward emission of microwave energy from said microwave antenna.

10. The tissue ablation apparatus of claim 9, wherein said microwave shield entirely surrounds said elongated microwave antenna.

11. The tissue ablation apparatus of claim 9, further comprising a microwave energy conducting cable connected to said elongated microwave antenna.

12. The tissue ablation apparatus of claim 9, wherein said tubular metal support has a curvature across its length, and further comprising a metal cover having substantially the same curvature as said tubular support curvature, disposed to partially cover said elongated end effector antenna.

13. The tissue ablation apparatus of claim 9, further comprising a metal cover disposed to completely cover said first microwave absorbing material.

* * * * *